United States Patent
Karim et al.

(10) Patent No.: US 10,914,689 B2
(45) Date of Patent: Feb. 9, 2021

(54) METHOD AND SYSTEM FOR HIGH-RESOLUTION X-RAY DETECTION FOR PHASE CONTRAST X-RAY IMAGING

(71) Applicant: KA IMAGING INC., Kitchener (CA)

(72) Inventors: Karim S. Karim, Waterloo (CA); Christopher C. Scott, Waterloo (CA)

(73) Assignee: KA IMAGING INC., Waterloo (CA)

(*) Notice: Subject to any disclaimer, the term of this patent is extended or adjusted under 35 U.S.C. 154(b) by 0 days.

(21) Appl. No.: 16/050,354

(22) Filed: Jul. 31, 2018

(65) Prior Publication Data

US 2019/0113466 A1 Apr. 18, 2019

Related U.S. Application Data

(60) Provisional application No. 62/597,622, filed on Dec. 12, 2017, provisional application No. 62/573,759, filed on Oct. 18, 2017.

(51) Int. Cl.
*A61B 6/00* (2006.01)
*G01N 23/00* (2006.01)
*G01N 23/041* (2018.01)

(52) U.S. Cl.
CPC .......... *G01N 23/041* (2018.02); *A61B 6/482* (2013.01); *A61B 6/484* (2013.01); *A61B 6/5205* (2013.01); *A61B 6/542* (2013.01)

(58) Field of Classification Search
CPC ............................. G01N 23/041; A61B 6/484
See application file for complete search history.

(56) References Cited

U.S. PATENT DOCUMENTS

| 5,440,130 A * | 8/1995 | Cox ...................... G01T 1/2018 250/370.09 |
| 7,412,026 B2 | 8/2008 | Liu et al. |
| 8,588,366 B2 | 11/2013 | Mukaide et al. |
| 2007/0238957 A1* | 10/2007 | Yared .................... A61B 5/0059 600/407 |
| 2008/0013683 A1 | 1/2008 | Shinden et al. |
| 2008/0217559 A1* | 9/2008 | Poglitsch ............. G01N 23/046 250/491.1 |
| 2010/0111395 A1 | 5/2010 | Tamakoshi |
| 2011/0282181 A1* | 11/2011 | Wang .................... A61B 5/0095 600/407 |
| 2012/0106698 A1* | 5/2012 | Karim .................. A61B 6/4241 378/37 |
| 2015/0139397 A1* | 5/2015 | Smith ..................... H04N 5/32 378/62 |

OTHER PUBLICATIONS

Canadian Intellectual Property Office as International Searching Authority, International Search Report for PCT/CA2018/050931, dated Nov. 2, 2018.
Canadian Intellectual Property Office as International Searching Authority, Written Opinion for PCT/CA2018/050931, dated Nov. 2, 2018.

* cited by examiner

*Primary Examiner* — Dani Fox
(74) *Attorney, Agent, or Firm* — Gowling WLG (Canada) LLP; Jeffrey W. Wong

(57) ABSTRACT

A phase contrast X-ray imaging system for imaging an object including an X-ray source; and an X-ray detector having a 25 micron or less pixel pitch; wherein a distance between the X-ray source and the object is less than or equal to 10 cm.

18 Claims, 10 Drawing Sheets

METHOD AND SYSTEM FOR HIGH-RESOLUTION X-RAY DETECTION FOR PHASE CONTRAST X-RAY IMAGING

CROSS-REFERENCE TO RELATED APPLICATIONS

This application claims the benefit of priority of U.S. Provisional Patent Applications No. 62/573,759 filed Oct. 18, 2017 and 62/597,622 filed Dec. 12, 2017 which are hereby incorporated by reference.

FIELD OF THE DISCLOSURE

The disclosure is generally directed at X-ray imaging and, more specifically, at a method and system for a high-resolution X-ray detection for phase contrast imaging.

BACKGROUND OF THE DISCLOSURE

X-ray imaging has far-reaching applications in visualizing objects using contrast provided by the heterogenous x-ray absorption of their composition. Naturally, the utility of this dominant paradigm of x-ray imaging diminishes if the penetrating power of x-rays effectively make the object transparent. Such is often the case for soft biological tissues or other low-density materials such as plastics. In this context, we recall from optics that electromagnetic waves have both an amplitude and a phase associated with them. As x-rays penetrate the object, information is not only encoded in the amplitude due to absorption, but also in the phase due to refraction. This is analogous to a lens in optics, where it is essentially transparent, however the refraction of visible light encodes the shape of the lens. X-ray phase contrast imaging (XPC) comprises methods of extracting phase information from the x-ray intensity pattern detected by the detector.

The more practical solutions proposed to date for XPC involve the use of multiple X-ray gratings and interferometry techniques (i.e. Talbot Lau) which reduce the dose efficiency, worsen spatial resolution, and increase cost and complexity of the imaging chain making the entire system bulky and not suitable for low-cost compact applications (e.g. benchtop XPC). All but the simplest method, propagation-based XPC (PB-XPC), requires additional apparatus.

Using PB-XPC, the ability to retrieve phase information, that is to detect the very small refraction angles of x-rays, falls entirely on the capabilities of the x-ray source. To date, PB-XPC is a common technique used at synchrotron facilities where the following three critical requirements are simultaneously met for PB-XPC: (1) monochromatic X-rays to facilitate ease of image reconstruction, (2) spatially coherent X-rays that can provide a correlated wave-field from which to detect phase changes and (3) since spatial coherence is proportional to the source-to-object distance, a high flux of X-rays is necessary because the object is placed far from the source and X-ray intensity is inversely proportional to the square of the distance. Although the PB-XPC technique has proven to be useful, it is practically limited to use at synchrotron facilities. Thus, there is still a need for a compact and fast X-ray phase contrast imaging system for home lab life sciences, health and scientific imaging, and non-destructive test applications that is based on PB-XPC but does not require a synchrotron source to successfully image low density materials at low X-ray exposures.

Therefore, there is provided a novel method and system for high-resolution X-ray detection for phase contrast imaging

SUMMARY OF THE DISCLOSURE

In one aspect of the disclosure, there is provided a phase contrast X-ray imaging system for imaging an object including an X-ray source; and an X-ray detector having a 25 micron or less pixel pitch; wherein a distance between the X-ray source and the object ($R_{1-1}$) is less than or equal to 10 cm.

In another aspect, $R_{1-1}$ is a distance between a source focal point of the X-ray source and an object plane of the object. In a further aspect, a distance between the X-ray detector and the object ($R_{2-1}$) is greater than 0 cm. In yet another aspect, $R_{2-1}$ is a distance between an object plane of the object and a detector plane of the X-ray detector. In an aspect, $R_{2-1}$ is less than or equal to 200 cm.

In a further aspect, the system further includes a second X-ray source; and a second X-ray detector; wherein a distance between the second X-ray source and the object ($R_{1-2}$) is less than or equal to 10 cm. In another aspect, a distance between the second X-ray detector and the object ($R_{2-2}$) is greater than 0 cm. In another aspect, the X-ray source and the second X-ray source shine X-ray beams towards the object in non-parallel directions. In yet a further aspect, the X-ray source and the second X-ray source shine X-ray beams towards the object in perpendicular directions. In an aspect, a focal spot of the X-ray source is <30 μm. In another aspect, the X-ray detector is a multi-layer X-ray detector. In yet another aspect, the multi-layer X-ray detector includes direct conversion layers. In another aspect, the multi-layer X-ray detector includes direct and indirect conversion layers. In yet another aspect, the multi-layer X-ray detector includes indirect conversion layers.

In another aspect of the disclosure, there is provided a method of phase contrast X-ray imaging including placing an X-ray source a distance $R_1$ away from an object to be imaged; placing an X-ray detector a distance $R_2$ away from the object to be imaged; directing a polychromatic beam at the object via the X-ray source; and detecting the X-ray photons via the X-ray detector; wherein the X-ray detector includes pixels having a size less than or equal to 25 microns; and wherein $R_1$ is less an 10 cm. In another aspect, $R_2$ is between 0 cm and 200 cm.

In another aspect of the disclosure, there is provided a phase contrast X-ray imaging system for imaging an object including an X-ray source; and an X-ray detector; wherein a distance between the X-ray source and the object ($R_1$) is less than or equal to 10 cm; and wherein a distance between the X-ray detector and the object ($R_2$) is between 0 and 200 cm.

In another aspect, $R_1$ is measured between an output of the X-ray source and an object plane of the object. In yet another aspect, $R_2$ is measured between a detector plane of the X-ray detector and an object plane of the object.

BRIEF DESCRIPTION OF THE DRAWINGS

Embodiments of the present disclosure will not be described, by way of example only, with reference to the attached Figures.

DETAILED DESCRIPTION OF THE DISCLOSURE

The disclosure is directed at a method and system for a high-resolution X-ray detection for phase contrast imaging. In one embodiment, the system includes an X-ray source and an X-ray detector with a pixel pitch of less than or equal to 25 microns. The X-ray source is preferably located a distance $R_1$ from an object plane while the X-ray detector is preferably located a distance $R_2$ from the object plane.

Figure 1:
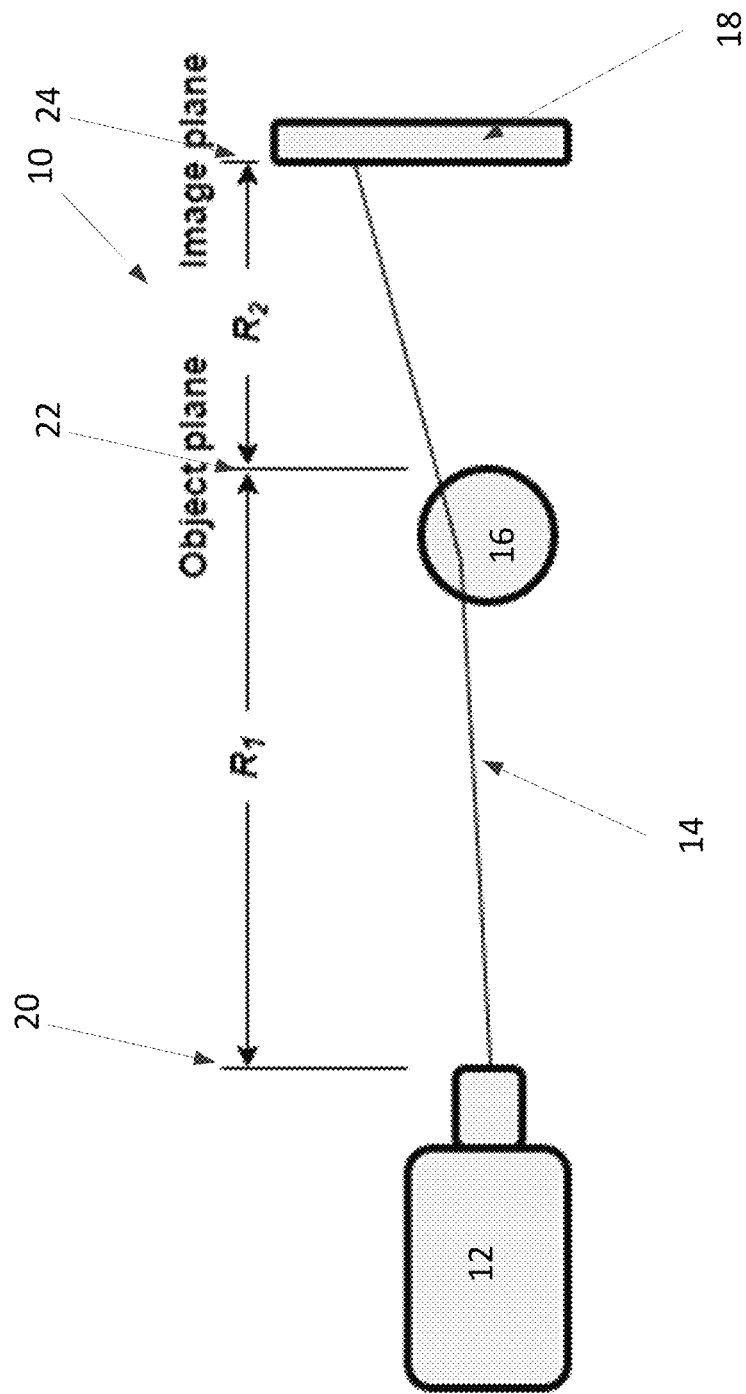
FIG. 1 is a schematic diagram of a propagation-based X-ray phase contrast imaging system.

Turning to FIG. 1, a schematic diagram of a system for high-resolution X-ray detection for phase contrast imaging is shown. The system may be seen as a propagation-based X-ray phase contract imaging system. In one embodiment, the system enables propagation-based X-ray phase contrast imaging (PB-XPC) in a compact, fast manner by approaching PB-XPC from a source and detector perspective. The system 10 includes an X-ray source 12 that directs X-rays (such as in the form of a polychromatic beam 14) towards an object 16 that is being imaged. The system further includes a detector 18, located on a side opposite the X-ray source with respect to the object 16) to receive, or detect, the X-rays that pass through the object 16 through free-space propagation. In a preferred embodiment, the X-ray source 12 is a standard laboratory micro-focus source and the X-ray detector 18 is a very high resolution and dose efficient X-ray detector having a pixel pitch of less than or equal to 25 microns.

As shown in FIG. 1, an output plane 20 of the focal spot of the X-ray source 12 is located a distance $R_1$ from the object plane 22 while an image plane 24 of the X-ray detector 18 is a distance $R_2$ from the object plane 22. By selecting a corresponding pixel pitch (preferably less than or equal to 25 microns), an optimal (or preferred) $R_1$ (which can be seen as an X-ray source focal spot to object plane/source to object distance) and an optimal (or preferred) $R_2$ (which may be seen as an object plane to detector image plane/object to detector distance) may be selected to achieve, fast, dose efficient PB-XPC using a benchtop device. In one embodiment, the selection of the pixel pitch may be based on the X-ray refraction angle of the X-ray leaving the object (calculated from the complex refractive index) and the propagation distance $R_2$. In a preferred embodiment, a small $R_2$ is more desirable, leading to a deviation of the X-ray on the that is detectable by a detector having pixels with a small pixel pitch (such as less than or equal to 25 microns).

As was experienced during experiments, the system may detect the minute (in the range of $10^{-5}$-$10^{-4}$ rad) X-ray refraction associated with phase changes encoded by the object 16.

In one preferred embodiment, the X-ray source 12 may be a standard low-power (8 W) laboratory micro-focus source with a focal spot size of 5 to 9 µm. The focal spot size is the size of the X-ray source electron beam that contacts the anode target materials e.g. tungsten or molybdenum, which then produces X-rays that propagate to the object 16 and subsequently to the detector 18). In current medical imaging solutions, the focal spot size is 0.3 to 1 mm. When the focal spot is small (such as between 5 to 9 µm), the penumbral blur from the extent of the focal spot is minimized or reduced such that that the X-ray source 12 does not limit spatial resolution within the system 10. Given the aim to detect phase changes due to the object 16, a coherent or partially coherent incident beam is necessary or preferred. The lateral coherence length is proportional to the source-to-object distance, $R_1$, and inversely proportional to the focal spot size. That is, a smaller focal spot results in a partially coherent beam with a smaller $R_1$ distance, or in other words, a more compact system.

One challenge is that a small focal spot in a traditional fixed anode (i.e. not a costly liquid-metal jet source), the micro-focus source results in low power output due to the heat load on the object. This limitation is a key challenge in obtaining a phase contrast image in both a short time and at low x-ray exposures (e.g. to minimize or reduce radiation damage to objects such as, but not limited to, biological samples).

Figure 2:
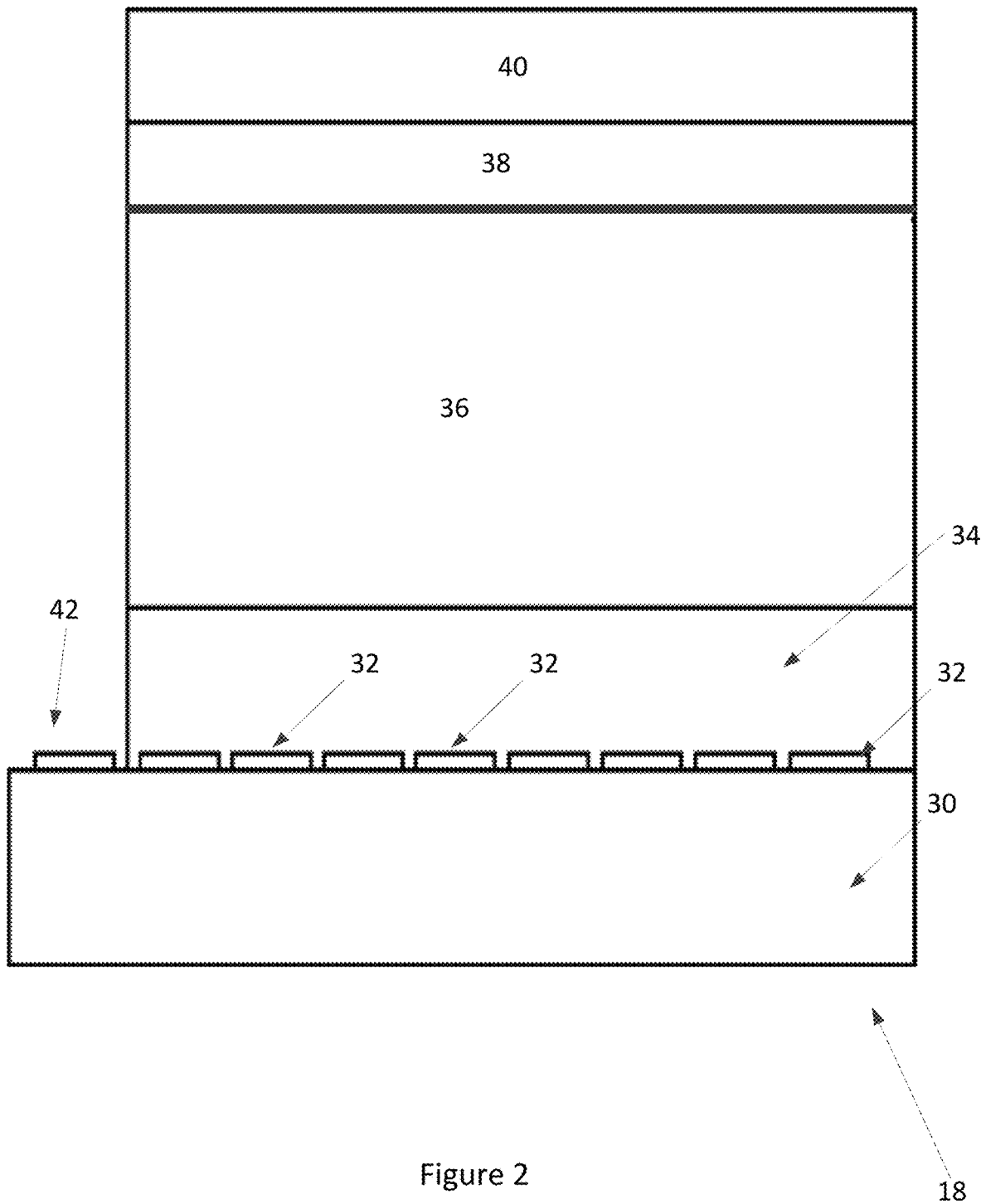
FIG. 2 is a schematic diagram of a cross-section of the direct-conversion x-ray detector.

Turning to FIG. 2, a schematic cross-section of an X-ray detector is shown. In the current disclosure, the detector is preferably a high-resolution x-ray detector based using a direct conversion photoconductor and complementary metal-oxide semiconductor (CMOS) pixel electronics having a pixel pitch of less than or equal to 25 microns.

As shown in FIG. 2, the X-ray detector 18 includes a bottom CMOS layer 30 with a plurality of small sized pixels 32. In the current disclosure, the pixel pitch of each of the pixels 32 is less than or equal to twenty-five (25) microns. The detector 18 further includes a stability/blocking layer 34, a photoconductor layer 36, a blocking layer 38 and an electrode layer 40. The detector 18 may further include a set of bond pads 42 that are used to enable an electrical connection for control/data signals.

In one embodiment, the photoconductor layer 36 is an amorphous selenium (a-Se) photoconductor layer 36. In this embodiment, the blocking layers 34 and 38 on either side of the a-Se photoconductor layer 36 may be used to improve mechanical stability of the detector 18 and/or to reduce the dark current during operation of the detector 18 at high electric fields. In another embodiment, the detector 18 may include only one or none of the blocking layers 34 or 38.

In another embodiment, the stability/blocking layer 34 may be a polyimide layer that may function as both, an anticrystallization layer and as a blocking contact on the bottom of the photoconductor layer 36. In another embodiment, the blocking layer 38 may be a parylene layer that functions as a blocking contact for the photoconductor layer 36. A contact layer between the photoconductor layer 36 and the stability/blocking layer may also be, but is not limited to, a p-type layer (such as As-doped selenium) or other soft polymer materials. A contact layer between the photoconductor layer 36 and the blocking layer 38 may also be, but is not limited to, a n-type layer such as alkali-metal-doped selenium or cold deposited selenium, or other known organic and inorganic hole blocking layers. Although the previous discussion relates to a direct conversion X-ray detector, other high-resolution detector technologies, such as indirect conversion detectors, or a combination of direct conversion and indirect conversion X-ray detectors are contemplated.

In direct conversion X-ray detectors, amorphous selenium, silicon, CdZnTe, CdTe, $HgI_2$, PbO, and scintillator infused organic photoconductors such as perovskite integrated with CMOS or thin-film-transistor (TFT) pixel arrays may be used for the photoconductor layer 36. With indirect conversion X-ray detectors, CsI, $LaBr_3$, and pixelated GOS or CsI scintillators integrated CMOS or TFT pixel arrays are may be used.

Excluding x-ray obliquity, which affects both indirect and direct conversion detectors, the thickness of the direct conversion photoconductor within the X-ray detector does not have the same trade-off with spatial resolution as an indirect conversion photoconductor because a large applied electric field transports the X-ray generated charge carriers with negligible lateral diffusion.

One advantage of the disclosure is the use of a very fine, or small, pixel pitch, high dose efficiency direct conversion X-ray detector to work in conjunction with the micro-focus source 12 for the PB-XPC approach.

Current X-ray indirect-detection technology exhibits a tradeoff between spatial resolution and dose efficiency. The scintillator material used to convert x-rays to optical photons for detection by a pixelated matrix of photodiodes results in increased optical scatter with thickness. Thicker scintillators absorb more photons but also lead to increased light scattering while thin scintillators preserve resolution by limiting scatter but absorb fewer photons and are dose inefficient reducing the detective quantum efficiency (DQE). Moreover, trying to visualize very fine features with lower spatial resolution detectors requires a large magnification factor which, when coupled with micro focal spot (and thus, lower power) X-ray sources additionally leads to longer scan times and dose.

Figure 3:
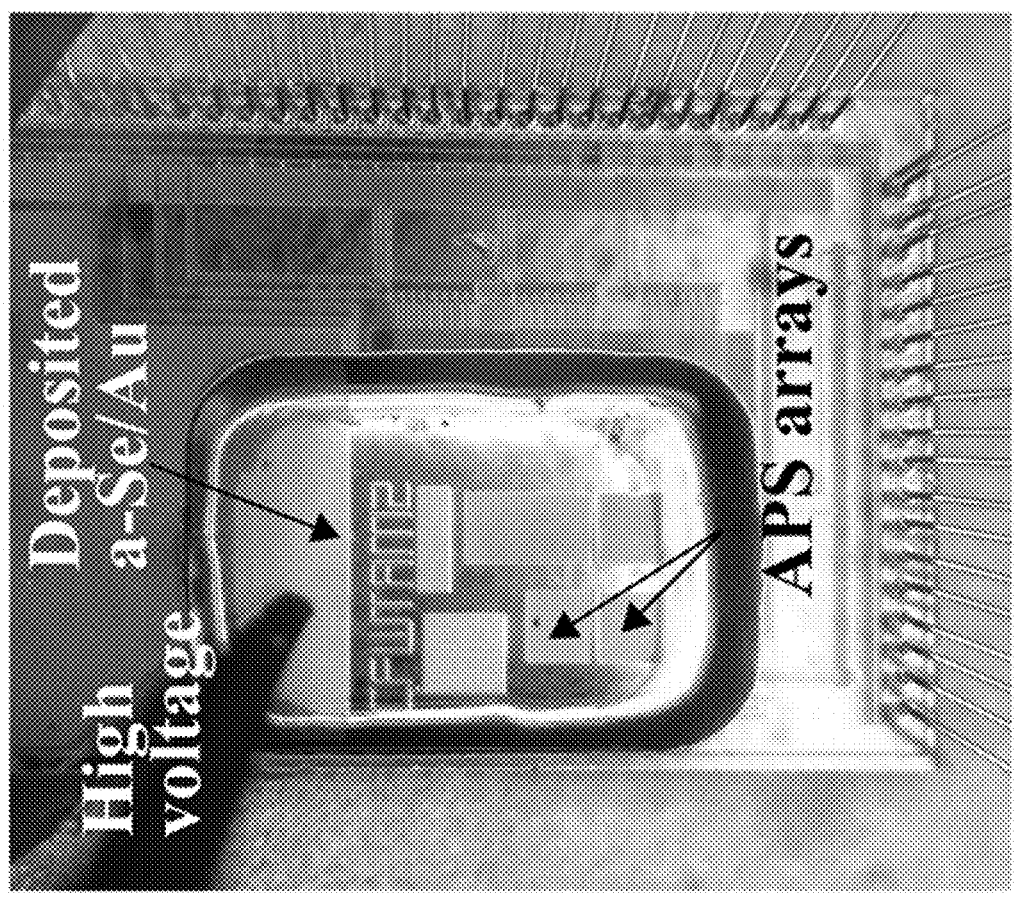
FIG. 3 is a photograph of a digital X-ray detector for use in the system of FIG. 1.

Turning to FIG. 3, a photograph of one embodiment of a pixel pitch imager is shown. The pixel pitch imager of FIG. 3 is a 5.5 um×6.25 um pixel pitch imager. Through experimentation, the dose efficiency measurements were around 10× better than current systems and projected results that may be up to 100× better than current detectors by using pixels having a size less than or equal to 25 microns. Imaging time can be further reduced by using high output micro-focus X-ray tubes (e.g. metal jet X-ray) as the X-ray source, however, use of a high dose efficiency detector helps further reduce imaging time (e.g. for high throughput industrial applications) and more importantly, to minimize or reduce further radiation damage to sensitive biological tissue, especially in life sciences and medical applications.

Furthermore, in the micrograph of FIG. 3, the pixel imager, or hybrid a-Se/CMOS digital X-ray detector, the overall chip dimensions are 1.8×3.0 $mm^2$. The a-Se/CMOS hybrid structure is visible with a biasing probe for application of positive high voltage to the gold electrode.

Figure 4A:
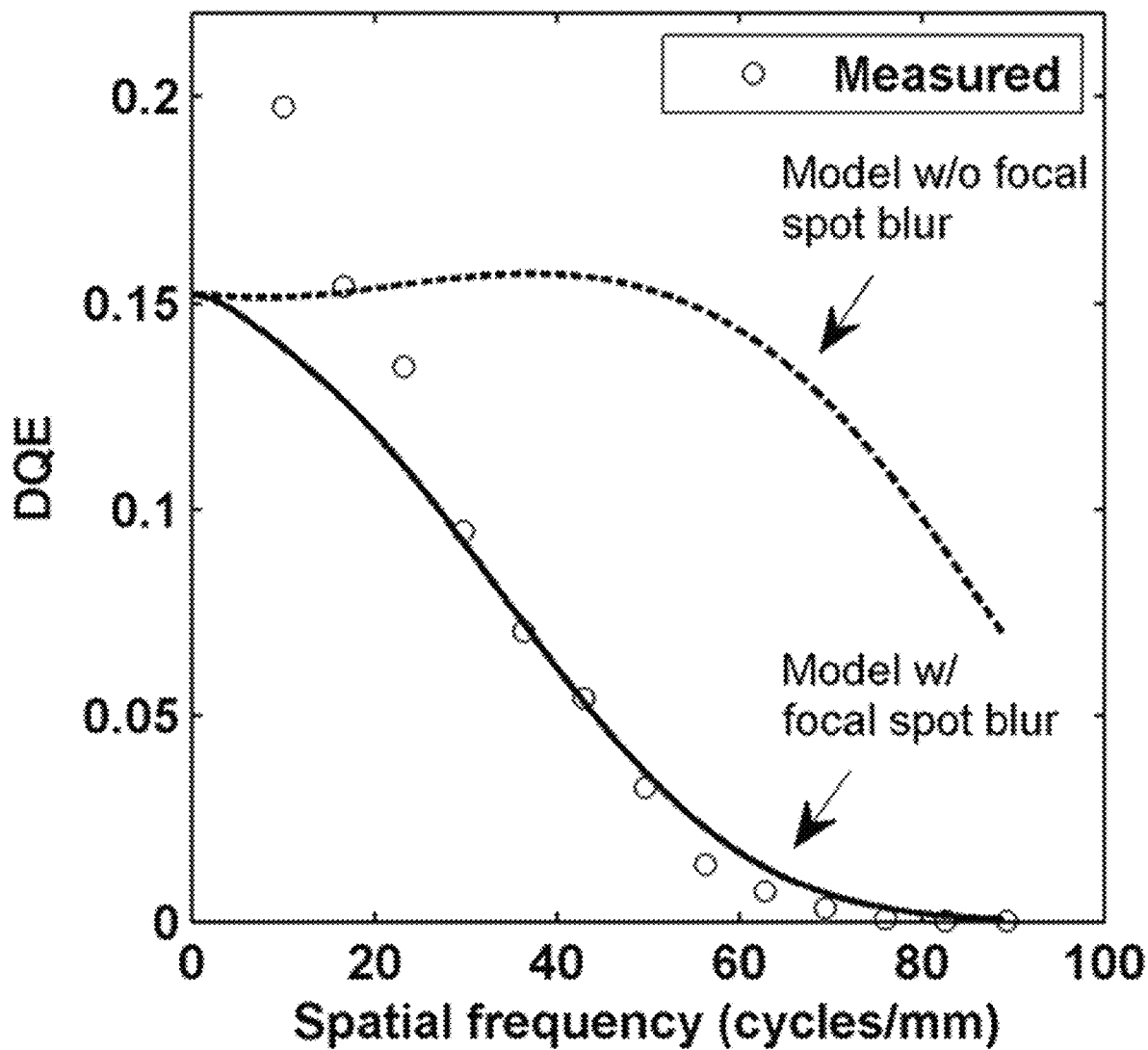
FIG. 4a is a graph showing DQE vs spatial frequency using the X-ray detector of FIG. 3.

In FIG. 4a, which reflect results/measurements using the X-ray detector of the disclosure, the DQE calculated for the 70 kVp spectrum using the measured modulation transfer function (MTF) and measured noise power spectrum (NPS) are shown. The results in the 20-60 cycles/mm range exceed all other previously reported X-ray detector DQE results.

Figure 4B:
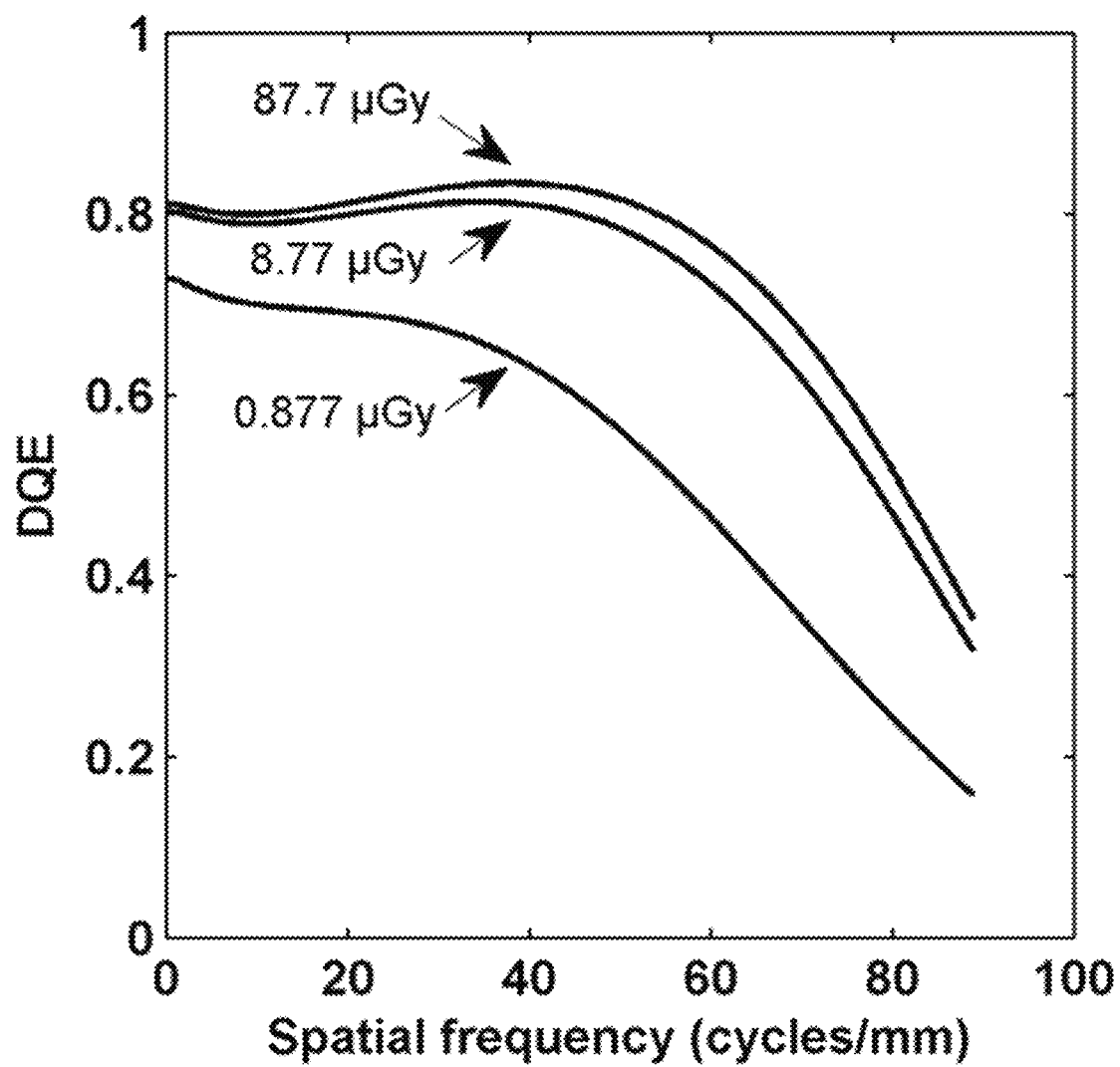
FIG. 4b is a graph showing DQE vs spatial frequency using known X-ray detectors.

FIG. 4b shows a modeled DQE at 70 kVp for an absorption-optimized a-Se photoconductor layer with a thickness of 1000-μm assuming no focal spot blur and 100 $e^-$ RMS read-out noise. With optimized X-ray absorption, the DQE is very high (above 0.5 or 50%) in the 20-60 cycles/mm range. For the graph of FIG. 4b, the photoconductor thickness for the modelled detector is 1000 microns while the photoconductor thickness for the detector of FIG. 4a was 56 microns.

Figure 5B:
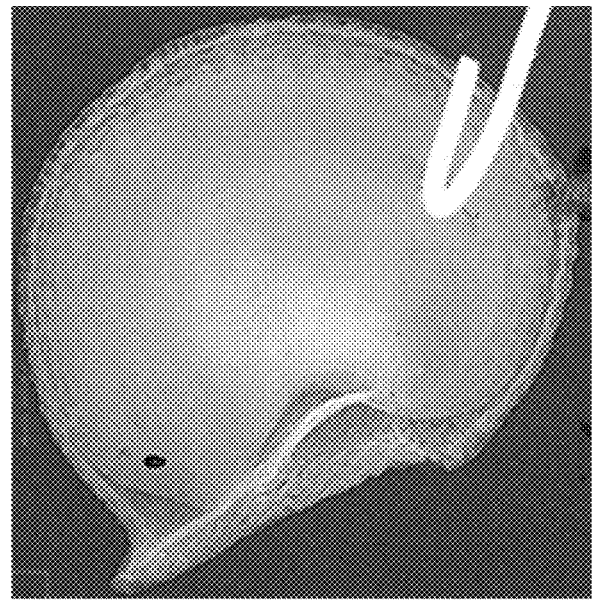
FIG. 5b is an X-ray image of a bell-pepper seed absorption image with phase contrast.
Figure 5A:
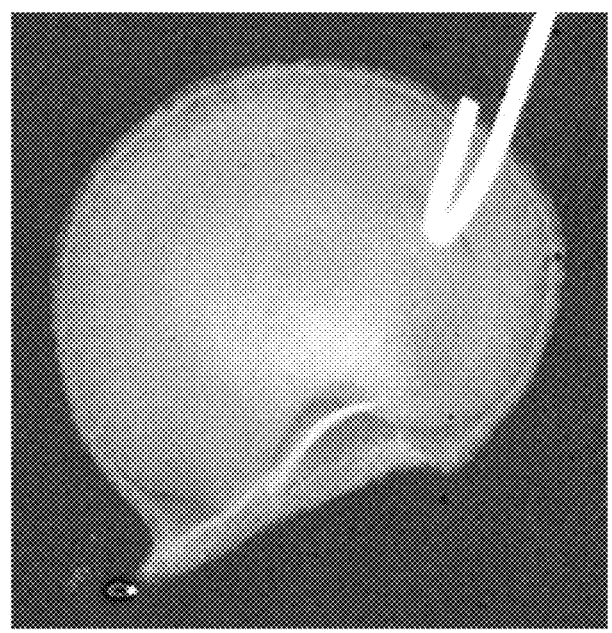
FIG. 5a is an X-ray image of a bell-pepper seed absorption image with phase contrast reduced.

Using the phase contrast X-ray system of the disclosure, the added detail due to phase contrast is demonstrated in FIGS. 5a and 5b. The hook was used to suspend the bell pepper seed which served as the object being imaged. In the case of this phase contrast image, the source-to-detector distance was 26 cm (sum of $R_1+R_2$), allowing the images to be taken in a few seconds compared to the minutes and hours commonly reported for current phase contrast systems. As such, the system of the disclosure may be seen as a highly compact, fast, low dose PB-XPC systems. In this experiment, $R_1$ was less than 10 cm for the images captured (with $R_2$ greater than 0 cm). The $R_1$ values used in the system of the disclosure are in direct contrast to current PB-XPC systems which teach away from using $R_1$ values of <10 cm.

Using the system of the disclosure, phase contrast images were achieved with $R_1$ values of <10 cm for a range of $R_2$ values (e.g. between 0 and 200 cm) and pixel sizes of less than or equal to 25 microns. In one embodiment, pixels sizes less than 10 microns are contemplated.

In simulations, a source focal spot of <30 μm was shown to be suitable for phase contrast imaging although a focal spot of <10 μm is preferable for sharper images and a more compact system.

Figure 6:
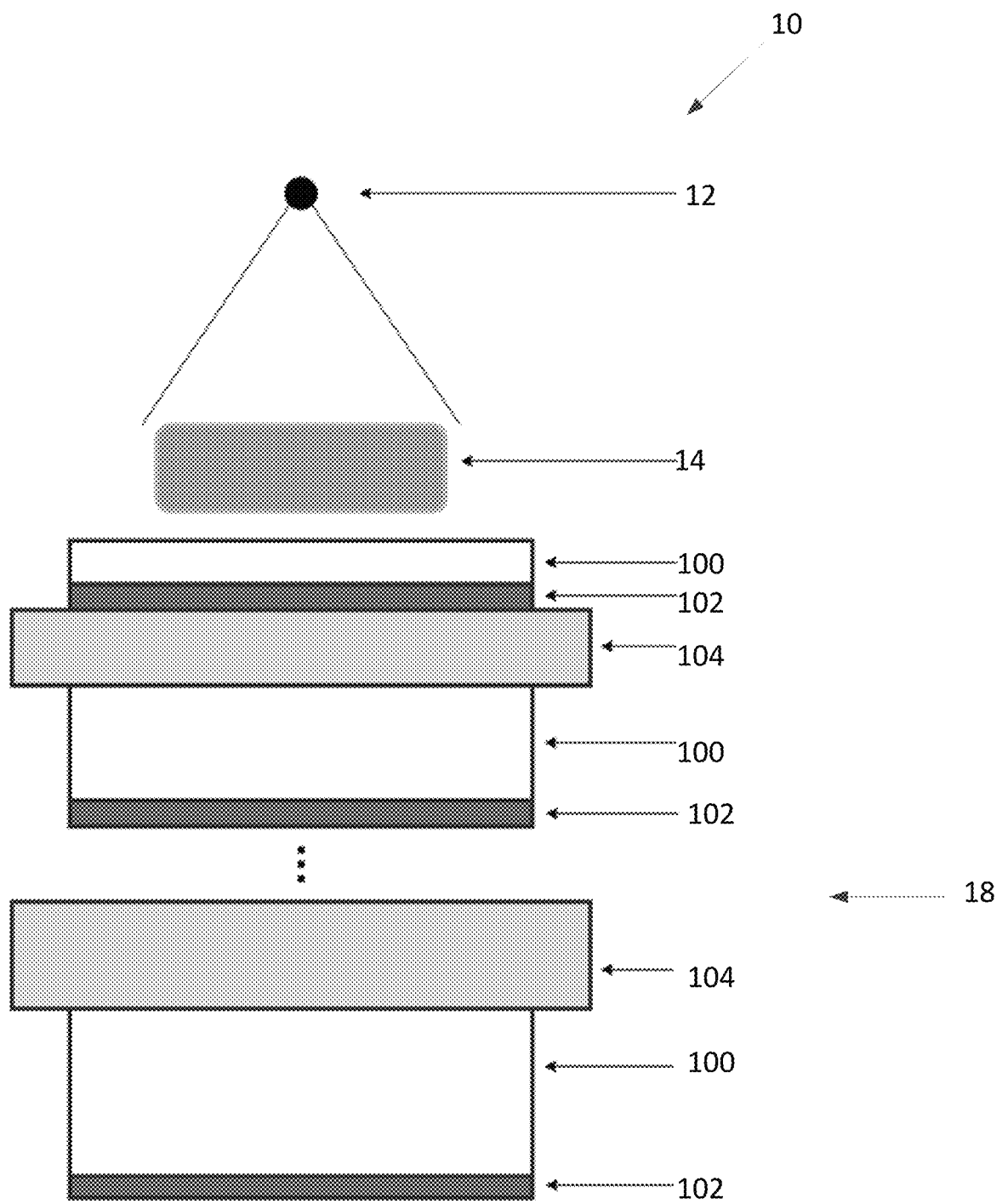
FIG. 6 is a schematic diagram of a multilayer detector having layers 1 to N.

Turning to FIG. 6, a diagram of another embodiment of an X-ray detector for use with the system of the disclosure is shown. The X-ray detector 18 of FIG. 6 may be seen as a multi-layer detector and may enable a compact X-ray imaging system that acquires both: multi-spectral (e.g. dual energy spectral X-ray data) as well as a phase contrast image (including phase retrieval) simultaneously.

In the current embodiment, the X-ray detector 18 includes a set of conversion layers 100 (seen as Conversion layer 1, Conversion layer 2, . . . Conversion layer N (where N is any number)) a set of substrate layers 102 and a set of X-ray filters 104. Different design/structure of the conversion layers 100, substrate layers 102 and X-ray filters 104 are contemplated and FIG. 6 provides one such example structure. As will be appreciated, the simplest implementation of such a multi-layer detector would include two stacked conversion layers 100 with an intermediate mid-filter 104. An improved approach could use three stacked conversion layers with the middle conversion layer acting as a mid-filter. As will be understood, each of the conversion layers is associated with a set of pixels having a size of less than or equal to 25 microns. With N conversion layers and N set of pixels, N unique data sets may be simultaneously obtained or generated at a low object dose i.e. multi-spectral, phase contrast, along with an original attenuation image.

In the Fresnel region, the "transport of intensity equation" (TIE) implies that contrast from intensity variations at the image plane is proportional to the propagation distance from the object plane and the spatial gradient of the phase distribution in the object plane. This differential phase contrast results in an "edge-enhancement" effect due to phase changes being most abrupt at the edges of the object where there is a rapid change in the refractive index. Although the use of PB-XPC X-ray imaging results in increased contrast at object boundaries for better detectability of materials with poor x-ray absorption, the relationship between the physical geometry of the object and its visualization in the image plane is more complicated.

Specifically, the boundaries in the image may not correspond exactly to boundaries in the object. To restore quantitative boundary information in the image, a "phase retrieval" reconstruction is typically required to be performed. One method for phase retrieval is a "direct approach" by solving the deterministic TIE for x-ray intensity and phase information in the object plane. Being non-iterative and numerically efficient this method is viable for use in projection imaging and for 3D micro-CT.

The TIE, for a single wavelength, includes one known variable (intensity in the image plane) and two unknown variables (intensity and phase in the object plane). In the case of a pure phase (i.e. no absorption) or homogenous object and monochromatic radiation, the solution to the TIE is relatively straightforward. For this case, in the geometric optics approximation, the intensity and phase in the object plane are related and a unique solution to the TIE can be obtained from a single measurement in the image plane or alternately, a single image acquisition.

For general inhomogeneous objects (i.e. the more practical situation) with uncorrelated absorption and refraction properties, at least two measurements at different image planes or different radiation wavelengths are required to solve the system of equations. This requirement poses a challenge for radiation dose sensitive (life sciences or medical) or even high throughput (e.g. real-time) applications where the time taken to move the detector to acquire the two measurements (i.e. images) necessary for phase retrieval is prohibitive. As such, the system of the disclosure allows for multiple images to be retrieved with a lower dose exposure for the object. Moreover, most practical applications (e.g. biomedical clinical imaging or even in industrial inspection) require the use of commonly available polychromatic x-ray sources, which makes obtaining the conventional TIE solution problematic since it inherently assumes a monochromatic source.

To overcome the above challenges of obtaining at least two measurements to solve the TIE with monochromatic and/or polychromatic sources, the multilayer (i.e. stacked) X-ray detector of FIG. 6 may be used to simultaneously capture multiple images at different image planes with adaptable X-ray spectra for PB-XPC. A multilayer detector typically includes a plurality of stacked x-ray conversion layers on optional substrates with optional intermediate x-ray filter materials (such as schematically shown in FIG. 6), where critically, each conversion layer captures information in a different image plane.

Each conversion layer can be a direct conversion layer (such as the proposed fine pitch a-Se direct conversion X-ray detector) or an indirect conversion layer. In a direct conversion layer, an X-ray semiconductor (e.g. amorphous selenium, silicon, PbO, HgI2, CdZnTe, CdTe, organic semiconductor with nanoparticles, etc.) converts incident X-ray photons directly into electronic charge. The X-ray semiconductor can be optionally paired with a readout electronics plane (e.g. thin film transistor array, CMOS pixel array) that contains an active matrix array of readout pixels (transistors and/or storage capacitor). In certain cases, the X-ray semiconductor and readout electronics plane are both part of the X-ray conversion layer.

In an indirect X-ray conversion layer, the scintillator material (e.g. GOS, CsI, NaI, CaWO4, LYSO, etc.) is used to convert incident X-ray photons into optical photons, which are then detected by an underlying pixelated photosensitive readout electronics plane. The photosensitive readout electronics plane could be a large area active matrix array of pixels (e.g. containing a photodiode with thin film transistors or a photodiode with an active pixel sensor) made of a variety of materials including large area thin film inorganic (e.g. amorphous silicon, metal oxide, LTPS, continuous grain silicon, crystalline silicon) or even organic semiconductors. In this embodiment, the scintillator and photosensitive readout electronics can both be part of the X-ray conversion layer.

Figure 8:
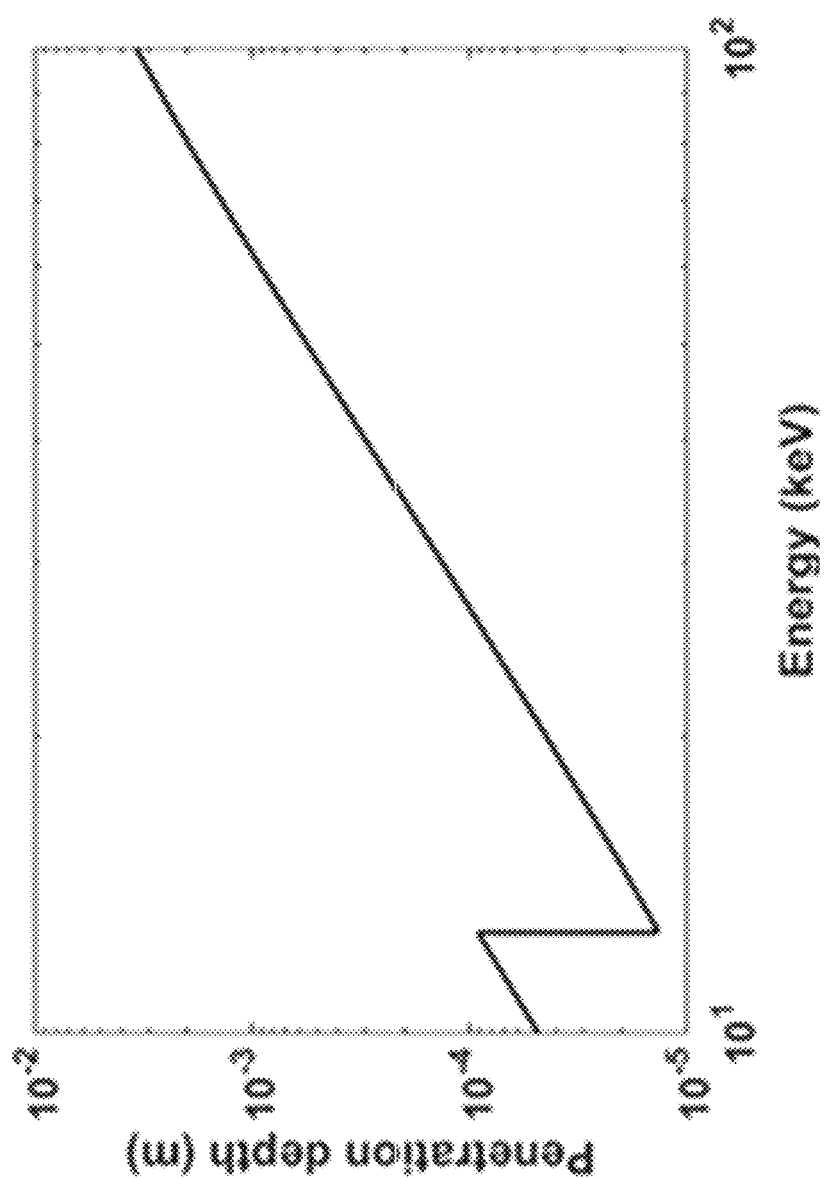
FIG. 8 is a graph showing penetration depth of x-ray photons in amorphous selenium photoconductor material.

Due to the greater penetration depth of higher energy photons relative to lower energy photons (e.g. see FIG. 8 for penetration depth in amorphous selenium semiconductor), a single x-ray exposure results in each X-ray conversion layer acquiring an image with a different x-ray spectrum. The X-ray spectra can be controlled using the thickness of each conversion layer (i.e. the semiconductor layer in direct conversion or the scintillator layer in indirect conversion) and/or the filter layer. Characterization of the spectra (without an object) may be necessary for phase retrieval.

In one embodiment, the penetration depth is equal to the reciprocal of the X-ray attenuation coefficient and corresponds to the depth within a material that the x-ray intensity reduces to ~37% of its initial value. The discontinuity at ~12.7 keV is due to photoelectric absorption.

Filter materials can range from common metal mid-filters, such as aluminum and copper. If an additional X-ray conversion layer is used as the filter, then, in this case, there would be three X-ray conversion layers stacked on top of each other. In principle, at least two X-ray conversion layers are necessary but additional layers can be stacked as necessary to obtain additional spectral separation, which could improve phase retrieval by allowing the use of more accurate reconstruction formulae.

Even further spectral separation could be obtained by modulating the X-ray semiconductor thickness in any given direct X-ray conversion layer on a pixel by pixel basis or alternately, modulating the scintillator thickness in any given indirect X-ray conversion layer on a pixel by pixel basis. By modulating the thickness of the X-ray conversion layer at the pixel level, spatial resolution can be a trade-off to obtain extra spectral separation even in a single layer.

Using very small pixel pitch dimensions (as with our fine pixel pitch detector having pixel sizes less than or equal to 25 microns) in each conversion layer can further improve performance by detecting the small refraction angle of x-rays (which is necessary for phase contrast) at shorter propagation distances from object plane to image plane. X-ray intensity (and therefore signal-to-noise ratio) decreases with the inverse square of propagation distance, so reducing propagation distance can lower dose as well as potentially speed up phase retrieval compared to other propagation-based methods or other phase contrast imaging modalities (e.g. grating based.)

Figure 7:
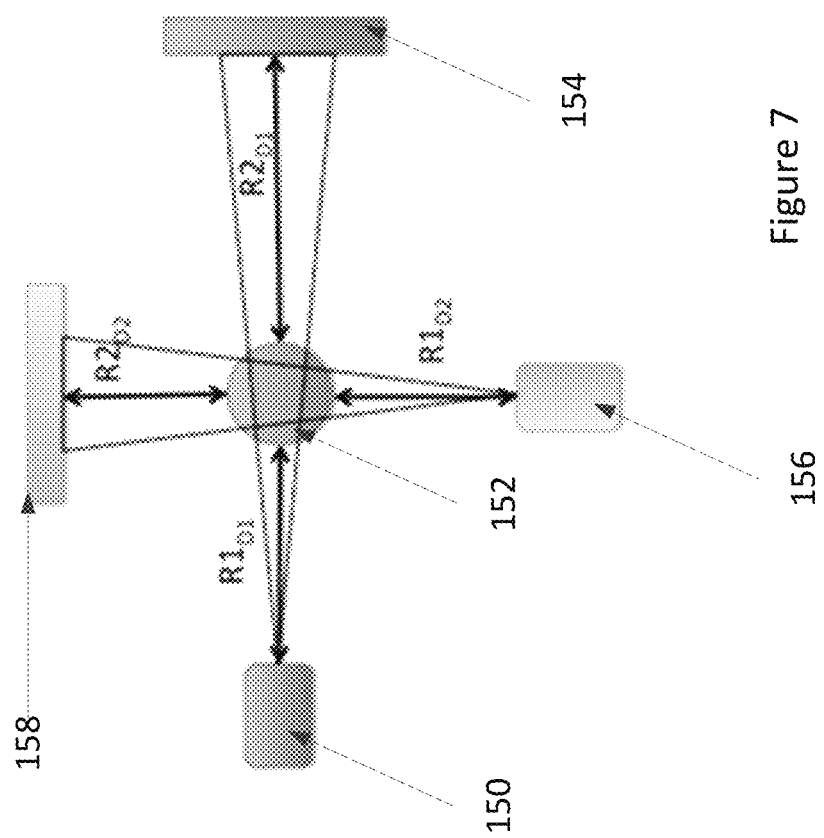
FIG. 7 is a schematic diagram of a first embodiment of a system configuration to obtain multi-energy X-ray images and phase contrast images simultaneously.

In another embodiment, to obtain both multi-spectral and phase retrieval data for PB-XPC, the system may include two different X-ray sources in conjunction with two fine-pitch single layer X-ray detectors that are operating in different planes as schematically shown in FIG. 7. As will be understood, a fine-pitch single layer X-ray detector is one with pixels having a size less than or equal to 25 microns.

As shown in FIG. 7, the system includes a first X-ray source 150 that directs a polychromatic beam towards an object 152 that is then detected by a first X-ray detector 154. The system further includes a second X-ray source 156 that directs a polychromatic beam towards the object 152 that is then detected by a second X-ray detector 158. In one embodiment, the distance between the first X-ray source 150 and the object plane ($R1_{D1}$ or $R_{1-1}$) and the distance between the second X-ray source 156 and the object plane ($R1_{D2}$ or $R_{1-2}$) may be set to the same value while the distance between the object plane and the image plane of the first X-ray detector 154 ($R2_{D1}$ or $R_{1-2}$) and the distance between the image plane of the second X-ray detector 158 and the object plane ($R1_{D2}$ or $R_{2-2}$) may be set to different values. The two set of X-ray source and X-ray detector pairs allow the system to obtain multiple two-dimensional (2D) images from the first and second X-ray detectors. In an alternate embodiment, the beams of the first X-ray source and the second X-ray source shine X-ray are directed towards the object in non-parallel directions. In another embodiment, the beams of the first X-ray source and the second X-ray source are directed towards the object in perpendicular directions.

In both embodiments where multiple images are generated or detected, they may then be combined in any known methodologies to obtain a single overall image (if required) using reconstruction algorithms.

One advantage of the system of FIG. 7 is that the X-ray spectrum from the first X-ray source 150 and the X-ray spectrum from the second X-ray source 156 may be defined independently of the first X-ray detector 154 and the second X-ray detector 158 leading to additional simplicity in the reconstruction algorithms. As before, the system configuration of FIG. 7 may enable acquisition of phase contrast images, phase retrieval, multi-spectral images and conventional attenuation images in a single scan. To obtain a three-dimensional (3D) image, either the object or the source/detector pairs can be rotated to obtain multiple projections for reconstruction or further X-ray source/X-ray detector pairs may be used.

Figure 9:
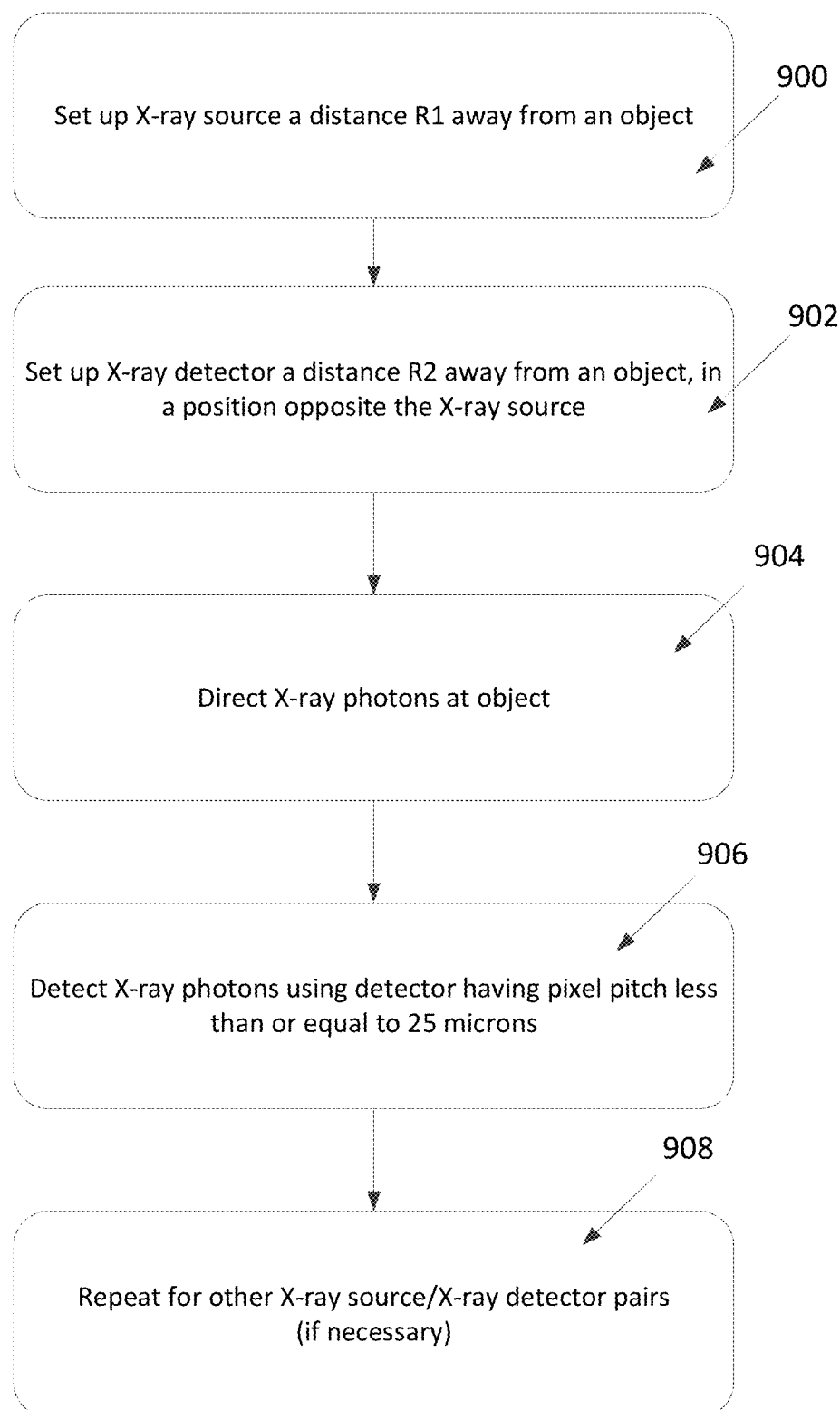
FIG. 9 is a flowchart outlining a method of phase contrast X-ray imaging.

Turning to FIG. 9, a flowchart outlining a method of phase contrast imaging is shown. Initially, an X-ray source is placed a distance $R_1$ away from the object being imaged (900). This distance is preferably less than 10 cm and, in one embodiment, is measured from the focal spot of the X-ray source to the object plane of the object. An X-ray detector is then placed a distance $R_2$ from the object (902) on a side of the object opposite the location of the X-ray source. This distance is preferably between 0 cm and 200 cm and, in one embodiment, is measured from the object plane to a detector plane.

The X-ray source then directs a polychromatic beam towards the object (904). The resulting photons are then detected by the X-ray detector via its set of pixels that are sized to be less than or equal to 25 microns (906). If necessary, further X-ray source and X-ray detector pairs may be placed (908) around the object to obtain multiple images with a lower radiation dose.

While the current disclosure has been directed at a compact phase contrast X-ray detector with direct conversion selenium-CMOS detectors, other direct conversion materials such as $HgI_2$, CZT, TIBr, and silicon can be employed in place of selenium and the CMOS pixels could be replaced by poly-Si, metal-oxide, or common II-VI or III-V semiconductors. Moreover, high-resolution indirect-conversion X-ray detectors (e.g. with thin scintillators, or pixelated scintillators) can also be employed albeit likely with lower dose efficiency than direct conversion detectors. Micro-computed-tomography (microCT) is also possible with this system by adding a rotational stage (or creating a rotating gantry) for generating multiple x-ray projection images of the object from different perspectives, and CT reconstruction software.

In addition to providing fast imaging in a compact system, the system of the disclosure also has a significant benefit for micro-anatomical imaging to visualize greater level of detail and avoid damaging DNA by using less X-ray radiation to acquire an image. As an example, since detailed knowledge of genes and the ability to control gene expression is available in mice and rats, the ability to quantitate the impact of highly targeted genetic manipulations on organ structure and function using phase contrast micro-CT could help answer how genes link to whole body pathophysiology. The combination of better visualization of soft tissue using phase contrast X-ray and high detector dose efficiency can fundamentally advance genomics by allowing high resolution, non-invasive and non-destructive imaging in live, intact animals and plants, tissues, and even single cells—tasks that are not possible using other techniques. Similar advantages exist for other scientific and non-destructive imaging applications for example, imaging agricultural products, plastics, polymers and various nano-composite materials and glasses.

In the preceding description, for purposes of explanation, numerous details are set forth in order to provide a thorough understanding of the embodiments. However, it will be apparent to one skilled in the art that these specific details may not be required. In other instances, well-known structures may be shown in block diagram form in order not to obscure the understanding. For example, specific details are not provided as to whether elements of the embodiments described herein are implemented as a software routine, hardware circuit, firmware, or a combination thereof.

Embodiments of the disclosure or components thereof can be provided as or represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor or controller to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor, controller, or other suitable processing device, and can interface with circuitry to perform the described tasks.

The above-described embodiments are intended to be examples only. Alterations, modifications and variations can be effected to the particular embodiments by those of skill in the art without departing from the scope, which is defined solely by the claims appended hereto.

We claim:

1. A phase contrast X-ray imaging system for imaging an object comprising:
    an X-ray source; and
    a X-ray detector having a pixel pitch less than 25 microns;
    wherein the X-ray detector includes at least one single direct conversion layer to acquire at least one phase contrast edge-enhancement image;
    wherein a distance (R1-1) between a source focal point of the X-ray source and an object plane of the object is greater than 1 cm and less than or equal to 10 cm;

wherein a distance (R2-1) between a detector plane of the X-ray detector and the object plane of the object is greater than 0 cm and less than or equal to 200 cm; and wherein a focal spot of the X-ray source is less than or equal to 10 μm.

2. The phase contrast X-ray imaging system of claim 1 further comprising:
a second X-ray source; and
a second X-ray detector.

3. The phase contrast X-ray imaging system of claim 2 wherein a distance (R1-2) between the second X-ray source and the object is less than 10 cm.

4. The phase contrast X-ray imaging system of claim 2 wherein a distance (R2-2) between the second X-ray detector and the object is greater than 0 cm.

5. The phase contrast X-ray imaging system of claim 4 wherein the X-ray source and the second X-ray source shine X-ray beams towards the object in non-parallel directions.

6. The phase contrast X-ray imaging system of claim 5 wherein the X-ray source and the second X-ray source shine X-ray beams towards the object in perpendicular directions.

7. The phase contrast X-ray imaging system of claim 1 wherein the X-ray detector is a multi-layer X-ray detector.

8. The phase contrast X-ray imaging system of claim 7 wherein the multi-layer X-ray detector comprises at least three direct conversion layers.

9. The phase contrast X-ray imaging system of claim 8 where the multi-layer X-ray detector comprises direct and indirect conversion layers.

10. The phase contrast X-ray imaging system of claim 1 wherein the phase contrast X-ray detector has a 20 micron or less pixel pitch.

11. The phase contrast X-ray imaging system of claim 10 wherein the phase contrast X-ray detector has a 15 micron or less pixel pitch.

12. The phase contrast X-ray imaging system of claim 11 wherein the phase contrast X-ray detector has a 10 micron or less pixel pitch.

13. The phase contrast X-ray imaging system of claim 1 wherein the focal spot of the X-ray source is less than or equal to 5 μm.

14. A method of phase contrast X-ray imaging comprising:
placing an X-ray source a distance R1 away from an object to be imaged, the X-ray source having a focal spot less than 10 μm;
placing an X-ray detector a distance R2 away from the object to be imaged;
directing a polychromatic beam at the object via the X-ray source;
detecting the X-ray photons via the X-ray detector; and
acquiring at least one phase contrast edqe-enhancement image;
wherein the X-ray detector includes pixels having a pitch size less than 25 microns; and
wherein R1 is less than or equal to 10 cm and greater than 1 cm and R2 is greater than 1 cm.

15. The method of claim 14 wherein R2 is between 1 cm and 200 cm.

16. A phase contrast X-ray imaging system for imaging an object comprising:
an X-ray source; and
a X-ray detector having a pixel pitch less than 25 micron and at least one direct conversion layer to acquire at least one phase contrast edge-enhancement image;
wherein a distance (R1) between the X-ray source and the object is less than or equal to 10 cm and greater than 1 cm; and
wherein a distance (R2) between the X-ray detector and the object is between 0 and 200 cm.

17. The phase contrast X-ray imaging system of claim 16 wherein R1 is measured between the focal spot of the X-ray source and an object plane of the object.

18. The phase contrast X-ray imaging system of claim 16 wherein R2 is measured between a detector plane of the X-ray detector and an object plane of the object.

* * * * *